United States Patent [19]
Pozzo et al.

[11] Patent Number: 5,604,280
[45] Date of Patent: Feb. 18, 1997

[54] RING SPIRO [FLUORENE-[2H]-BENZOPYRANES] AND THEIR USE IN OPHTHALMIC OPTICS

[75] Inventors: Jean L. Pozzo; Robert Guglielmetti; André Samat; Vladimir Lokshin; Guenaëlle Harie, all of Marseille, France

[73] Assignee: Essilor International Compagnie Generale D'Optique, Cedex, France

[21] Appl. No.: 417,321

[22] Filed: Apr. 5, 1995

[30] Foreign Application Priority Data

Apr. 6, 1994 [FR] France ................... 94 04028

[51] Int. Cl.$^6$ ............ C07D 311/96; C07D 311/92; C08K 5/3495; C08K 5/15
[52] U.S. Cl. ............ 524/110; 351/49; 351/166; 351/232; 428/29; 428/409; 524/90; 524/109; 546/28; 549/330; 549/24
[58] Field of Search ............ 524/109, 110, 524/90; 546/28, 39; 549/24, 330; 428/29, 409; 351/49, 166, 232

[56] References Cited

U.S. PATENT DOCUMENTS

| | | | |
|---|---|---|---|
| 5,066,818 | 11/1991 | Van Gemert et al. | 524/110 |
| 5,395,567 | 3/1995 | Van Gemert et al. | 524/110 |
| 5,451,344 | 9/1995 | Knowles et al. | 524/110 |

FOREIGN PATENT DOCUMENTS

| | | | |
|---|---|---|---|
| 562915 | 3/1993 | European Pat. Off. | 491/4 |
| 676401 | 10/1995 | European Pat. Off. | |
| 7-48363 | 2/1995 | Japan . | |

OTHER PUBLICATIONS

Meyer, Jean–Jacques et al "Upgrading . . . Compounds"—Analyst, Feb. 1995, pp. 447–452, vol. 120.
Dyes and Pigments, vol. 1, No. 2, 1980, London, G. B. pp. 139–159, H. Balli et al. "Photochrom Molekule: . . . ".
Chemical Abstracts, vol. 98, No. 26, 27 Juin 1983, Columbus, OH; Abstract No. 2251245, A. S. Kholmanskii, "Role of Vibrational Excitation in the Photocoloring of Spironaphthopyrans".
Molecular Photochemistry, vol. 1, No. 2, 1969, pp. 89–208. T. Bercovici et al. "Photochromism in Spiropyrans Part VIII. Photochromism in Acidified Solutions".

*Primary Examiner*—Veronica P. Hoke
*Attorney, Agent, or Firm*—Keck, Mahin & Cate

[57] ABSTRACT

The invention concerns photochromic compounds with general formula (I):

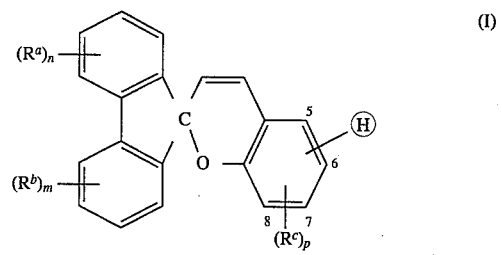

where $R^a$, $R^b$ and $R^c$ represent hydrogen; alkyl, aryl, OR, SR, COR or COOR, where R represents hydrogen, alkyl or aryl, amino with formula $NR_1R_2$, where $R_1$ and $R_2$ each represent hydrogen, alkyl, cycloalkyl, or aryl, $R_1$ and $R_2$ may together form a heterocycle containing four to seven members with the nitrogen atom and may intracyclically contain one or more heteroatoms selected from nitrogen, oxygen, sulphur, or a halogen atom; a mono- or polyhaloalkyl; an $NO_2$, CN or SCN group; n and m represent whole numbers from 1 to 4 depending on the number of substitutions on the nucleus and p is 1 or 2 depending on the number of substitutions on the nucleus; H is either an aromatic heterocycle condensed at the 5,6 or 6,7 positions, containing five or six members comprising one or more heteroatoms selected from nitrogen, selenium, oxygen and sulphur or an aromatic carbocycle containing five or six members, condensed at the 7,8 positions; all optionally substituted. The invention also relates to the use of these compounds in ophthalmic optics.

18 Claims, No Drawings

RING SPIRO [FLUORENE-[2H]-BENZOPYRANES] AND THEIR USE IN OPHTHALMIC OPTICS

The invention concerns novel photochromic compounds, in particular photochromic compounds containing a chromene nucleus with a spiro sp³ carbon and containing a fluorene nucleus, and their use in ophthalmics, in particular in and/or on ophthalmic lenses.

Photochromism is a phenomenon which has been known for a number of years. A compound is said to be photochromic when the compound, when irradiated with light, certain wavelengths of which are in the ultraviolet region, change colour and return to their original colour when irradiation ceases.

There are many applications of this phenomenon, but one of the most important applications is in ophthalmic optics.

These compounds can be used in manufacturing lenses for spectacles to filter light as a function of its intensity.

Incorporation of photochromic compounds into an organic material constituting an ophthalmic lens can produce a glass with considerably reduced weight with respect to conventional lenses of mineral glass which contain silver halides as the photochromic agent. Their incorporation into organic materials has always posed difficult technical problems.

However, not all photochromic compounds can perforce be used in ophthalmic optics. The photochromic compound must, in fact, satisfy a certain number of criteria, among them:

high colourability, the measure of the ability of a photochromic compound to produce an intense colour after isomerisation;

a colour after light absorption which renders the photochromic compound, either alone or combined with other photochromic compounds, suitable for use in ophthalmic glasses or lenses;

an absence of, or only slight, colouration in its initial form;

rapid colouration or decolouration kinetics;

photochromism occurring over the widest possible temperature range, in particular between 0° C. and 40° C.

Known organic photochromic compounds in current use generally exhibit decreasing photochromism with increasing temperature, such that photochromism is particularly marked at temperatures around 0° C., but is much weaker, even non-existent, at temperatures of the order of 40° C. which the glass can attain, in particular when exposed to sunshine.

A further problem with prior art photochromic compounds is their lifetime. Certain prior art products have been shown to have relatively short lifetimes. After a certain number of colouration and decolouration cycles, the photochromic compound generally transforms into oxidation products and no longer exhibits reversible photochromic properties.

A number of chromene type photochromic compounds have been synthesised. European patent application EP-A-0 246 114, for example, describes a series of photochromic compounds in which an adamantane group is introduced in position 2 of a benzopyrane or naphthopyrane nucleus, and International patent application WO 90/07507 describes two cyclopropyl groups attached at position 2 of a cyclic benzopyrane or naphthopyrane type compound. WO 91/00861 from the same inventor describes the introduction of a norcamphor or tricyclodecane group in position 2 of photochromic compounds of the same type.

U.S. Pat. No. 3,567,605 describes photochromic benzopyrane and naphthopyrane type. derivatives substituted in position 2 of the pyrane cycle. These compounds, however, have relatively slow kinetic decolouration constants.

Application EP-A-0 401 958 describes photochromic derivatives which also have low kinetic decolouration constants and which are less well adapted to the envisaged use.

In our French patent application FR-A-2 688 782, we have proposed heterocyclic benzopyrane photochromic compounds containing two phenyl groups in the 2 position of the benzopyrane cycle.

These compounds exhibit good colourability in the red region which allows them to be used in ophthalmic optics with photochromic compounds producing a blue colour, to produce a natural final colour when exposed to light. In addition, they exhibit an absence of colouration or a very slight colouration in the initial state and rapid colouration and decolouration kinetics at temperatures in the order of 0° C. to 40° C.

The applicant has surprisingly discovered a new group of heterocyclic chromenes containing a spiro carbon connected to a fluorene nucleus which exhibits particularly interesting photochromic properties. The spiro-fluorene compounds of the invention have a higher colourability in the red region than the 2,2-diphenyl-[2H]chromenes cited above.

The applicant has in fact discovered that the fluorene group causes a bathochromic shift (towards the red wavelengths) in the absorption spectrum of the coloured form compared with those of the 2,2-diphenyl-[2H]chromenes described previously.

Because of these properties, the compounds of the invention can be used in much lower quantities in ophthalmic optics with photochromic compounds producing a blue colour to produce a natural final colour when exposed to light.

The compounds of the invention also exhibit an absence of colouration or a very slight colouration in the initial state and rapid colouration and decolouration kinetics over a very wide temperature range, in particular between 0° C. and 40° C.

The applicant has also shown that these compounds have a particularly long lifetime.

These properties mean that these novel compounds are of particular interest when used in ophthalmic optics, in particular when used in and/or on ophthalmic lenses.

The term ophthalmic lenses within the context of the invention means spectacle lenses, in particular lenses for sunglasses, and contact lenses.

One object of the invention is thus to provide novel photochromic compounds.

Another object of the invention is constituted by their use in ophthalmic optics.

A further object of the invention is to provide compositions for use in coating ophthalmic lenses or incorporation into these lenses.

Further objects of the invention will become clear from the following description and examples.

The photochromic compounds of the invention are essentially characterised in that they have the following general formula (I):

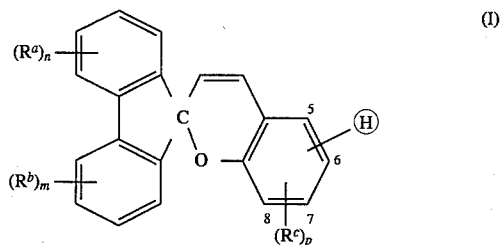

where $R^a$, $R^b$ and $R^c$ independently represent a hydrogen atom, an alkyl group, an aryl group, or an OR, SR, COR or COOR group, in which R represents a hydrogen atom, an alkyl group or an aryl group, an amino group with formula $NR_1R_2$, where $R_1$ and $R_2$ independently represent a hydrogen atom, an alkyl group, a cycloalkyl group, or an aryl group, $R_1$ and $R_2$ can form a heterocycle containing four to seven members with the nitrogen atom and may also contain one or more heteroatoms selected from nitrogen, oxygen and sulphur, a halogen atom, a mono- or polyhaloalkyl group; or an $NO_2$, CN or SCN group; n and m represent whole numbers from 1 to 4 depending on the number of substitutions in the nucleus and p is 1 or 2 depending on the number of substitutions in the nucleus; groups $R^a$ $R^b$ and $R^c$ can have different meanings when m, n and p are greater than 1 and depending on the position in the nuclei; H is an aromatic heterocycle containing five or six members, condensed at the 5,6 or 6,7 positions, containing one or more heteroatoms selected from oxygen, selenium, sulphur and nitrogen or an aromatic carbocycle containing five or six members, condensed at the 7,8 positions; said carbocycle or heterocycle H being able to be substituted by one or more alkyl, alkoxy, amino, aryl or aralkyl groups or condensed with a further cycle containing five to ten members.

In formula (I) above, the term alkyl group preferably means a group containing one to six carbon atoms; the cycloalkyl group preferably means a group containing three to seven carbon atoms; the aryl group preferably represents a phenyl group; halogen preferably represents chlorine, bromine or fluorene; and the polyhaloalkyl group preferably represents the $CF_3$ group.

The heterocyclic H nuclei condensed at the 5,6 or 6,7 positions on the benzopyrane nucleus are represented in particular by formula (II) or formula (III):

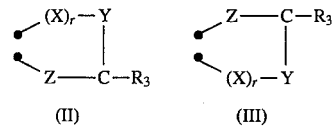

where:

X represents N or the $CR_4$ group, the nitrogen or carbon atom being bonded to the adjacent atom by a double bond to ensure aromaticity of the heterocycle condensed on the benzopyrane nucleus with formula (I), E is 0 or 1;

Y and Z independently represent $NR_5$, S, O, Se; or N or CR6, each being bonded to the adjacent atom by a double bond to ensure aromaticity of the heterocycle condensed on the benzopyrane nucleus, $R_5$ and $R_6$ independently represent a hydrogen atom, a $C_1$–$C_6$ alkyl group or a phenyl group;

$CR_3$ is bonded to an adjacent atom by a double bond to ensure aromaticity of the heterocycle condensed on the benzopyrane nucleus;

$R_3$ represents a hydrogen atom, a $C_1$–$C_6$ alkyl group or a phenyl group or forms with one of the $R_5$ or $R_6$ groups, a cycle C, which may or may not be aromatic, containing five to ten members, preferably six to seven members, which can optionally be substituted by one or more radicals $R^a$ as defined above.

One of groups X, Y and Z represents N, O, S, Se or $NR_5$.

In the above formula (II) or (III), preferred cycles C are selected from benzene, cyclohexane or cycloheptane.

Preferred heterocycles H with formula (II) or (III) are nuclei of pyrimidine, pyrazine, pyridine, oxazole, pyrrole, thiazole which may be substituted, or furans condensed with a cycle, such as benzofuran, cycloheptanofuran or cyclohexanofuran.

The spiro[fluorene-chromene] compounds of the present invention exhibit stronger colourability in the red region than their 2,2-diphenyl-[2H]chromene homologues. Compared with the diphenyl group, the fluorene nucleus induces a bathochromic shift of the corresponding maximum absorption band ($\lambda_1$) in the order of +10 nm to +30 nm.

A particularly interesting group of spiro[fluorenechromene] compounds of the invention is constituted by compounds with formula (I) where H is a heterocycle containing five members and is condensed at the 5,6 or 6,7 positions with the benzopyrane cycle. The coloured forms of these particular compounds have an absorption spectrum containing a new band corresponding to an absorption peak ($\lambda_3$) of the order of +500 nm.

Of the compounds in this group, those with formula (I) in which the heterocycle is condensed at the 6,7 position are more particularly preferred due to the ring formation in heterocycle H in the 6,7 position which broadens the principal band corresponding to ($\lambda_1$) with the appearance of a second absorption maximum ($\lambda_2$). In addition, ring formation in the 6,7 position of heterocycle H produces a shift of the second absorption band ($\lambda_3$) of 15 nm to 30 nm. Chromene compounds are thus produced in which the colouration, in the irradiated state, is further shifted towards the red and in which the intensity is substantially higher.

Examples of compounds with formula (I) used in the present invention are those with the following chemical formulae:

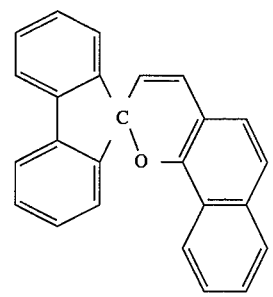

(A)

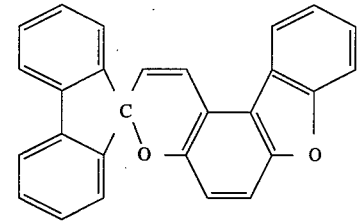

(B)

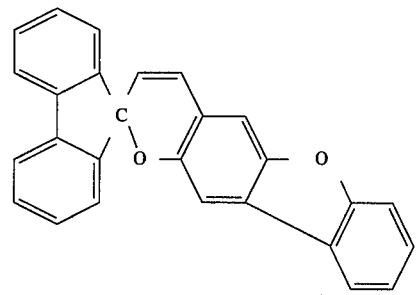

(C)

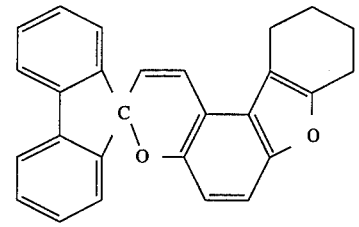

(D)

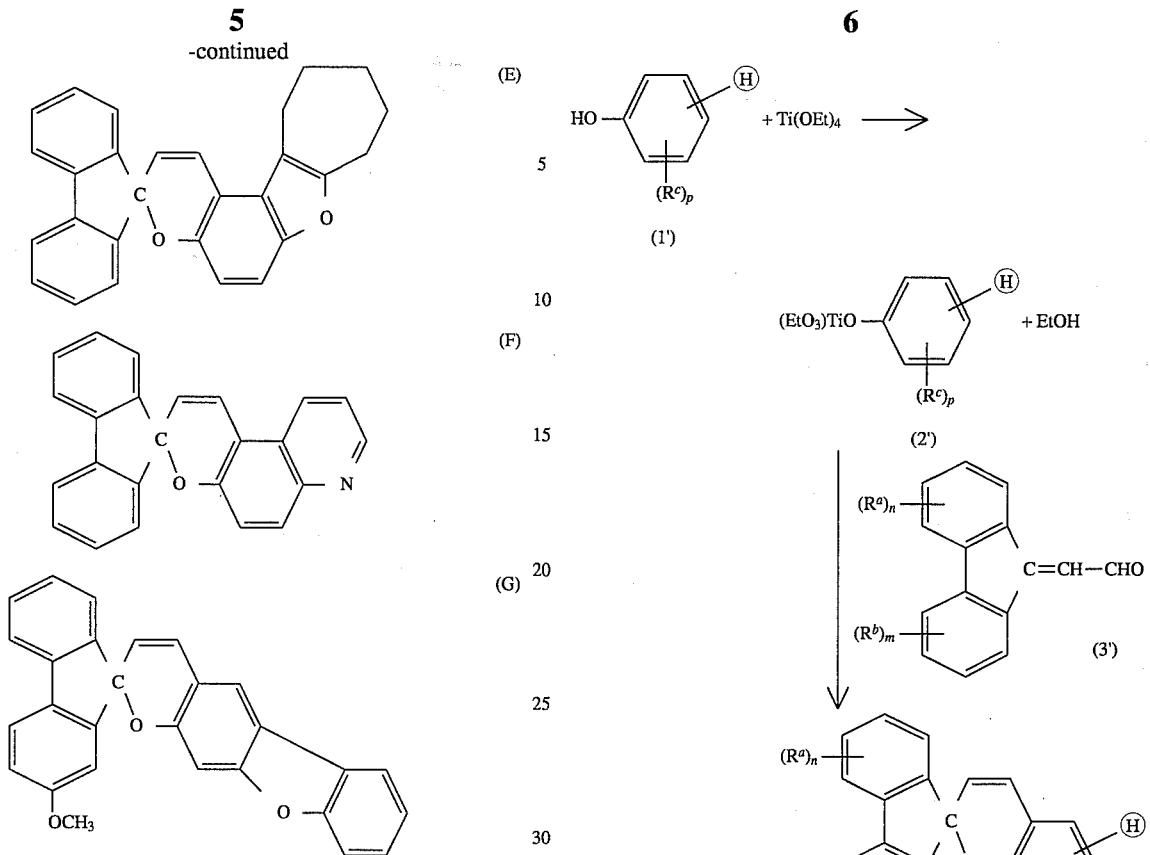

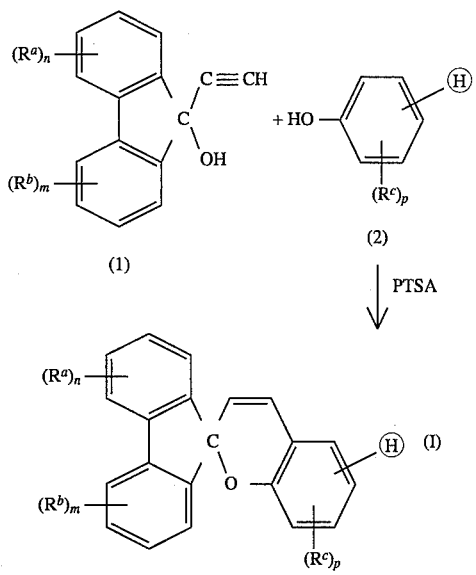

The compounds of the invention can be prepared by using the following reaction scheme:

In accordance with this reaction scheme, a derivative of 9-ethynyl 9-fluorenol with formula (1), where $R^a$, $R^b$, m and n have the meanings given above, is reacted with a phenol with formula (2) in which $R^c$, p and H have the meanings given above, in the presence of p-toluene sulphonic acid (PTSA). The compounds of the invention can also be prepared by using the following reaction scheme:

In this reaction scheme, in formulae (1'), (2') and (3'), radicals $R^a$, $R^b$, $R^c$ and m, n and p have the meanings given above.

The photochromic compounds of the invention can be used to produce photochromic ophthalmic lenses.

The compounds of the invention can be introduced into a composition for application to or introduction into a transparent organic polymeric material to produce a transparent photochromic article. They can also be introduced into solid compositions such as plastic films, plates and lenses to form materials for use as ophthalmic lenses, sunglasses, visors, film/video camera optics and filters.

Liquid compositions of the invention are essentially characterised in that they contain the compounds of the invention dissolved or dispersed in a medium based on solvents suitable for application to or introduction into a transparent polymeric material.

Particular solvents that can be used are organic solvents selected from benzene, toluene, chloroform, ethyl acetate, methyl ethyl ketone, acetone, ethyl alcohol, methyl alcohol, acetonitrile, tetrahydrofuran, dioxane, the methyl ether of ethylene glycol, dimethylformamide, dimethyl sulphoxide, methyl cellosolve, morpholine and ethylene glycol.

When the compounds of the invention are dispersed, the medium can also contain water.

In another embodiment of the invention, the compounds of the invention are introduced into and preferably dissolved in colourless or transparent solutions prepared from transparent polymers, copolymers or mixtures of polymers in an appropriate organic solvent.

Examples of these solutions are solutions of nitrocellulose in acetonitrile, polyvinyl acetate in acetone, polyvinyl chloride in methyl ethyl ketone, polymethyl methacrylate in acetone, cellulose acetate in dimethylformamide, polyvinyl pyrrolidone in acetonitrile, polystyrene in benzene, and ethyl cellulose in methylene chloride.

These compositions can be applied to transparent supports such as polyethylene glycol terephthalate, boryl-containing paper, or cellulose triacetate, and dried to obtain a photochromic material which colours in the presence of ultraviolet radiation and which returns to its colourless and transparent state in the absence of the radiation source.

The photochromic compounds of the present invention or the compositions containing them defined above can be applied to or incorporated into a solid transparent polymerised organic material which is suitable for ophthalmic elements such as ophthalmic lenses or materials which are suitable for use in sunglasses, visors, video/film camera optics and filters.

Examples of transparent solid materials which can be used to produce ophthalmic lenses according to the invention are polymers of polyol(allylcarbonate), polyacrylates, poly(alkylacrylate) compounds such as polymethyl methacrylates, cellulose acetate, cellulose triacetate, cellulose-acetate-propionate, cellulose-acetate-butyrate, poly(vinyl acetate), poly(vinyl alcohol), polyurethanes, polycarbonates, polyethylene terephthalates, polystyrenes, poly(styrene-methyl methacrylate) compounds, copolymers of styrene and acrylonitrile, and polyvinylbutyrates.

Transparent copolymers or mixtures of transparent polymers are also suitable for producing such materials.

Examples are materials prepared from polycarbonates such as poly(4,4'-dioxy-2,2-diphenolpropane), polymethyl methacrylate, polyol(allylcarbonate) compounds such as diethylene glycol bis(allylcarbonate) in particular, and its copolymers such as those with vinyl acetate. Particular examples are copolymers of diethylene glycol bis(allylcarbonate) and vinyl acetate (80–90/10–20) and the copolymer of diethylene glycol bis(allylcarbonate) with vinyl acetate, cellulose-acetate-propionate and cellulose-acetate-butyrate (80–85/15–20).

Polyol(allylcarbonate) compounds are prepared using allyl carbonates of aliphatic or aromatic linear or branched liquid polyols, such as aliphatic glycols of bis-allyl carbonate or alkylene bis(allylcarbonate) compounds. Examples of polyol(allylcarbonate) compounds which can be used to prepare solid transparent materials in accordance with the invention are ethylene glycol bis(allylcarbonate), diethylene glycol bis(2-methallylcarbonate), diethylene glycol bis(allylcarbonate), ethylene glycol bis(2-chloroallylcarbonate), triethylene glycol bis(allylcarbonate), 1,3-propanediol bis(allylcarbonate), propylene glycol bis(2-ethylallylcarbonate), 1,3-butanediol bis(allylcarbonate), 1,4-butanediol bis(2-bromoallylcarbonate), dipropylene glycol bis(allylcarbonate), trimethylene glycol bis(2-ethylallylcarbonate), pentamethylene glycol bis(allylcarbonate), and isopropylene bisphenol bis(allylcarbonate). The most important product is diethylene glycol bis(allylcarbonate), known under the trade name CR39.

The quantity of photochromic compounds of the invention used either in the composition, or when introduced into the solid support, is not critical and generally depends on the colour intensity which the composition can confer on the material following exposure to radiation. In general, the more photochromic compound added, the deeper the colouration when irradiated.

In accordance with the invention, a quantity sufficient to confer the treated material with the property of changing colour when exposed to radiation is used. This quantity of photochromic compounds is generally between 0.01% and 20% by weight, preferably between 0.05% and 10% by weight with respect to the total weight of the optical material or the composition.

The photochromic compounds of the invention can also be introduced in a temporary transfer support (such as a lacquer forming a coating on a substrate) and then thermally transferred into the substrate, in particular as described in patent U.S. Pat. Nos. 4,286,957 or 4,880,667.

These compounds can be used with other photochromic compounds such as photochromic compounds giving rise to different colourations such as blue or green, which are known in the art. Thus, spiro(indoline-oxazines), which are well known in the art, can be used.

Once applied to the ophthalmic materials or introduced into these materials, the appearance of a colouration can be seen following exposure to UV radiation, followed by a return to the original colour or transparency when exposure to UV radiation is halted.

The compounds of the invention have the advantage of allowing this colouration change many times at varying temperatures between 0° C. and 40° C.

The following examples illustrate the invention without in any way limiting its scope.

SYNTHESIS EXAMPLES

EXAMPLE 1

Spiro[fluorene-9,2'-[2H]naphtho[1,2-b]-pyrane]

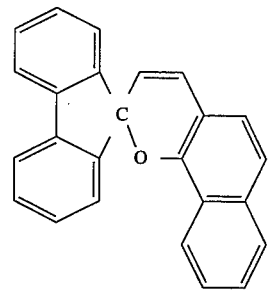

3.09 g of 9-ethynyl-9-fluorenol (15 mmoles) and 2.49 g of 1-naphthol (17.25 mmoles) were dissolved under reflux in 30 ml of anhydrous toluene in an inert atmosphere. 0.03 g of PTSA was then added. The reaction mixture was refluxed in an inert atmosphere for 2 hours 30 minutes. On returning to room temperature, the mixture was poured onto an aqueous 10% caustic soda solution. After decanting, the aqueous phase was continuously extracted with dichloromethane. The organic phases were combined and dried over magnesium sulphate. The solvent was removed under reduced pressure. The compound was precipitated out with hexane then recrystallised from toluene.

Yield 22%

Molecular weight 333.41 g

Melting point 137° C.

EXAMPLE 2

Spiro[3H-benzofurano[3,2-g]chromene-3,9'-fluorenel]

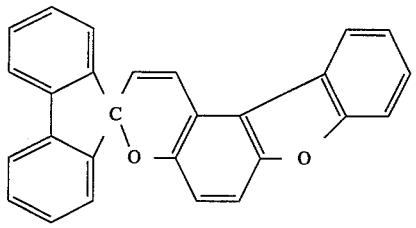

1.03 g of 9-ethynyl-9-fluorenol (5 mmoles) and 1.06 g of 2-hydroxy dibenzofuran (5.75 mmoles) were dissolved under reflux in 15 ml of anhydrous toluene in an inert atmosphere. 0.01 g of PTSA was then added. The reaction mixture was refluxed in an inert atmosphere for 2 hours. On returning to room temperature, the mixture was poured onto an aqueous 10% caustic soda solution. After decanting, the aqueous phase was continuously extracted with dichloromethane. The organic phases were combined and dried over magnesium sulphate. The solvent was removed under reduced pressure. The compound was purified by flash chromatography, using 99% pentane—1% ethyl ether as the eluent. The solid obtained after removal of the solvent under reduced pressure was then washed with hexane.

Yield 41%
Molecular weight 372.43 g
Melting point 151° C.

EXAMPLE 3

Spiro[7H-benzofurano[3,2-g]chromene-7,9'-fluorene]

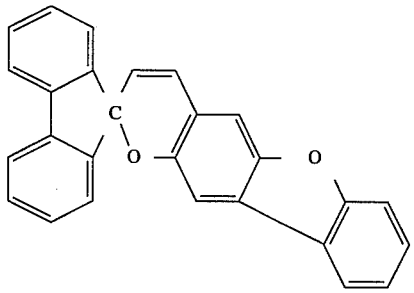

1.03 g of 9-ethynyl-9-fluorenol (5 mmoles) and 1.06 g of 2-hydroxy dibenzofuran (5.75 mmoles) were dissolved under reflux in 15 ml of anhydrous toluene in an inert atmosphere. 0.01 g of PTSA was then added. The reaction mixture was refluxed in an inert atmosphere for 2 hours. On returning to room temperature, the mixture was poured onto an aqueous 10% caustic soda solution. After decanting, the aqueous phase was continuously extracted with dichloromethane. The organic phases were combined and dried over magnesium sulphate. The solvent was removed under reduced pressure. The compound was purified by flash chromatography, using 98% pentane—2% ethyl ether as the eluent, then recrystallised several times from heptane.

Yield 21%
Molecular weight 372.43 g
Melting point 195° C.

EXAMPLE 4

8',9'-tetramethylene-spiro[fluorene-9,3'-[3H]-furano[3,2-f]chromene]

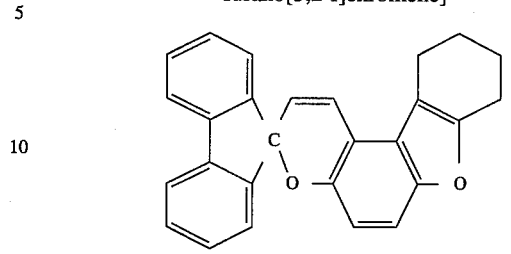

1.44 g of 9-ethynyl-9-fluorenol (7 mmoles) and 1.52 g of 2,3-tetramethylene-5-hydroxybenzofuran (8.05 mmoles) were dissolved under reflux in 20 ml of anhydrous toluene in an inert atmosphere. 0.015 g of PTSA was then added. The reaction mixture was refluxed in an inert atmosphere for 3 hours. On returning to room temperature, the mixture was poured onto an aqueous 10% caustic soda solution. After decanting, the aqueous phase was continuously extracted with dichloromethane. The organic phases were combined and dried over magnesium sulphate. The solvent was removed under reduced pressure. The compound was purified by flash chromatography (100% pentane). The compound was then recrystallised from a hexane-benzene mixture.

Yield 37%
Molecular weight 376.46 g
Melting point 201° C.

EXAMPLE 5

8',9'-pentamethylene-spiro[fluorene-9,3'-[3H]-furano[3,2-f]chromene]

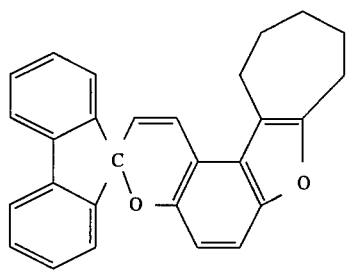

1.44 g of 9-ethynyl-9-fluorenol (7 mmoles) and 1.62 g of 2,3-pentamethylene-5-hydroxybenzofuran (8 mmoles) were dissolved under reflux in 20 ml of anhydrous toluene in an inert atmosphere. 0.015 g of PTSA was then added. The reaction mixture was refluxed in an inert atmosphere for 3 hours. On returning to room temperature, the mixture was poured onto an aqueous 10% caustic soda solution. After decanting, the aqueous phase was continuously extracted with dichloromethane. The organic phases were combined and dried over magnesium sulphate. The solvent was removed under reduced pressure. The compound was purified by flash chromatography (100% pentane). The compound was then recrystallised from a hexane-benzene mixture.

Yield 41%
Molecular weight 390.49 g
Melting point 189° C.

EXAMPLE 6

Spiro[fluorene-9,8'-[8H]-pyrano[3,2-f]quinoline]

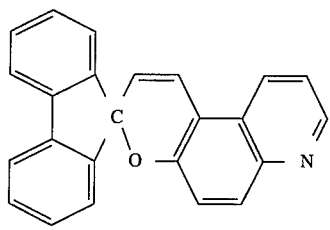

0.5 g of 6-hydroxyquinoline (3.4 mmoles) were dissolved at room temperature in 17 ml of anhydrous toluene in an inert atmosphere. A solution of 0.79 g of tetraethyl-orthotitanate (3.4 mmoles) dissolved in 4 ml of anhydrous toluene was added dropwise. The reaction mixture was refluxed in an inert atmosphere for 30 minutes. It was then distilled to remove the ethanol formed from the medium; the volume recovered was 7 ml. On returning to room temperature, a solution of 0.8 g of 9-fluoroenylidene acetaldehyde (3.9 mmoles) dissolved in 14 ml of anhydrous toluene was slowly added in an inert atmosphere. The reaction mixture was then refluxed for 2 hours. On returning the mixture to room temperature, the mixture was poured onto a 2M caustic soda solution. After decanting, the aqueous phase was continuously extracted with dichloromethane. The organic phases were combined and dried over magnesium sulphate. The solvent was removed under reduced pressure. The compound was purified by column chromatography (95% dichloromethane, 5% ethyl acetate). The compound was then recrystallised from dichloromethane.

Yield 62%

Molecular weight 333.39 g

Melting point 185° C.

EXAMPLE 7

2'-methoxy spiro[7H-benzofurano[3,2-g]chromene]-7,9'-fluorene

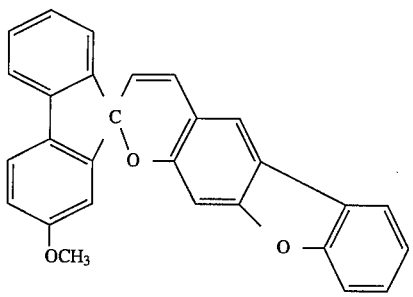

1.77 g of 9-ethynyl-2-methoxy-9-fluorenol (8 mmoles) and 1.52 g of 2-hydroxy dibenzofuran (8.1 mmoles) were dissolved at 60° C. in 20 ml of anhydrous toluene in an inert atmosphere. 0.019 g of PTSA was then added. The reaction mixture was left for 2 hours at 60° C. in an inert atmosphere. On returning to room temperature, the mixture was poured onto an aqueous 10% caustic soda solution. After decanting, the aqueous phase was continuously extracted with dichloromethane. The organic phases were combined and dried over magnesium sulphate. The solvent was removed under reduced pressure. The compound was purified by column chromatography (95% pentane, 5% diethyl ether). The compound was then recrystallised from heptane.

Yield 30%

Molecular weight 402.45 g

Melting point 176° C.

STUDY OF SPECTROKINETIC VALUES OF COMPOUNDS OF EXAMPLES 1 TO 7

Solutions in toluene of each of the compounds of Examples 1 to 4, at a concentration of $2.5 \cdot 10^{-5}$ M were irradiated with UV light.

The colourability $A_i$ of each solution was measured for the absorption maximum $\lambda_1$ in the absorption spectrum for each compound.

The different absorption maxima ($\lambda_1$, $\lambda_2$, $\lambda_3$) in each absorption spectrum were also measured (expressed in nm).

Measurements were carried out at 25° C. (±0.2° C., controlled by an external Hubert-ministat thermostat) in a cylindrical quartz cell with a 10 mm section and optical length of 10 cm.

The samples were photolysed using discharge tubes supplied by a battery of capacitors:

flash energy: of the order of 60 J, flash duration: 50 µs.

A represented the maximum optical density at time t of the solution after the flash, at a photochromic compound concentration in toluene of $2.5 \cdot 10^{-5}$ M.

The thermal decolouration kinetic constants $k_{66}$ (expressed in $s^{-1}$) and the corresponding amplitude of the thermal decolouration (expressed as a percentage) were measured, starting from the maximum colouration obtained after irradiation ($A_i$).

TABLE

| Example | $\lambda 1$ (nm) | A1 Colourability | $\lambda 2$ (nm) | A2 Colourability | $\lambda 3$ (nm) | A3 Colourability | Kinetic decolouration constants (decolouration amplitude) $\kappa_{A1}$ | $\kappa_{A2}$ |
|---|---|---|---|---|---|---|---|---|
| 1 | 409 | 0.70 | 436 | 0.94 | 495 | 1.44 | <0.001 | |
| 2 | 457 | 0.95 | | | 551 | 0.46 | 0.29 | 0.06 |

TABLE-continued

| Example | λ1 (nm) | A1 Colourability | λ2 (nm) | A2 Colourability | λ3 (nm) | A3 Colourability | Kinetic decolouration constants (decolouration amplitude) $\kappa_{A1}$ | $\kappa_{A2}$ |
|---|---|---|---|---|---|---|---|---|
| 3 | 460 | 1.75 | 491 | 1.82 | 569 | 0.75 | (35%) 0.52 | (65%) 0.01 |
| 4 | 447 | 1.26 | | | 534 | 0.39 | (65%) 0.34 | (35%) 0.017 |
| 5 | 449 | 1.33 | | | 535 | 0.41 | (40%) 0.30 | (60%) 0.02 |
| 6 | 443 | 0.75 | 475 | 0.9 | | | (45%) 0.19 | (55%) 0.05 |
| 7 | 458 | 1.55 | 492 | 1.76 | 566 | 0.70 | (55%) 0.66 | (45%) 0.014 |
| | | | | | | | (45%) | (55%) |

COMPARATIVE VISUAL TESTS

A visual colouration test was carried out on the photochromic solutions of the invention.

The test was carried out on solutions in toluene at a concentration of $2.5 \cdot 10^{-5}$ mole/l in quartz cells.

The samples were irradiated under the same conditions as those for measurement of the thermokinetic parameters.

Two prior art compounds from patent EP-A-0562915 were used as references:

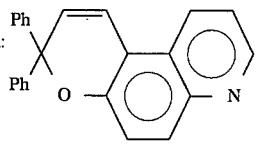

Compound A' with formula:

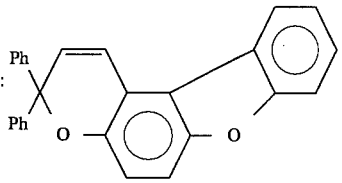

Compound B' with formula:

Samples of the photochromic compounds of the invention were compared with compounds A' and B'.

The colouration intensity after irradiation was visually adjudged:

+ corresponded to the colour of the reference compounds,

++ corresponded to a darker colouration than that of the reference compounds,

+++ corresponded to a much darker colouration than that of the reference compounds.

| Compound from example: | Colour observed | Intensity |
|---|---|---|
| 1 | red | +++ |
| 2 | dark red | ++ |
| 3 | pink-red | +++ |
| 4 | dark red | +++ |
| 5 | dark red | +++ |
| 6 | orange-red | ++ |
| 7 | pink-red | +++ |

-continued

| Compound from example: | Colour observed | Intensity |
|---|---|---|
| Reference compound: | | |
| A' | orange | + |
| B' | red | + |

We claim:

1. A photochromic compound with the following general formula (I):

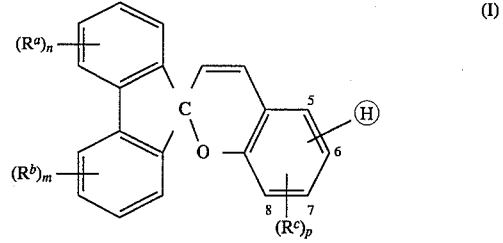

where $R^a$, $R^b$ and $R^c$ independently represent a hydrogen atom, an alkyl group, an aryl group, or an OR, SR, COR or COOR group, where R represents a hydrogen atom, an alkyl group or an aryl group, an amino group with formula $NR_1R_2$, where $R_1$ and $R_2$ independently represent a hydrogen atom, an alkyl group, a cycloalkyl group, or an aryl group, $R_1$ and $R_2$ can form a heterocycle containing four to seven members with the nitrogen atom and may also contain one intracyclic heteroatom selected from nitrogen, oxygen and sulphur, a halogen atom, a mono- or polyhaloalkyl group; an NO2, CN or SCN group; n and m represent whole numbers from 1 to 4 depending on the number of substitutions in the nucleus; and p is 1 or 2 depending on the number of substitutions in the nucleus; groups $R^a$, $R^b$ and $R^c$ can have different meanings when m, n and p are greater than 1 and depending on the position in the nuclei; H is an aromatic heterocycle containing five or six members, condensed at the 5,6 or 6,7 positions, containing one or more heteroatoms selected from oxygen, selenium, sulphur and nitrogen or an aromatic carbocycle containing five or six members, condensed at the 7,8 positions; said carbocycle or heterocycle H being able to be substituted by one or more alkyl, alkoxy, amino, aryl, or aralkyl groups or condensed with a further cycle containing five to ten members.

2. A compound according to claim 1 characterised in that in formula (I) the alkyl radical is a $C_1$–$C_6$ radical; the cycloalkyl radical contains three to seven carbon atoms; the aryl group is a phenyl group; the halogen represents chlorine, fluorine or bromine; and the polyhaloalkyl group is $CF_3$.

3. A compound according to claim 1 characterised in that the aromatic carbocycle H condensed at the 7,8 positions is a benzene cycle.

4. A compound according to claim 1 characterised in that the heterocycle H condensed at the 5,6 or 6,7 positions is selected from the following formulae:

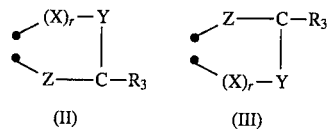

(II)   (III)

where:

X represents N or the $CR_4$ group, the nitrogen atom or the carbon atom being bonded to the adjacent atom by a double bond to ensure aromaticity of the heterocycle condensed on the benzopyrane nucleus with formula (I);

r is 0 or 1;

Y and Z independently represent NR5, S, O, Se; or N or CR6, each being bonded to the adjacent atom by a double bond to ensure aromaticity of the heterocycle condensed on the benzopyrane nucleus with formula (I), $R_5$ and $R_6$ independently represent a hydrogen atom, a $C_1$-$C_6$ alkyl group or a phenyl group;

$CR_3$ is bonded to an adjacent atom by a double bond to ensure aromaticity of the heterocycle condensed on the benzopyrane nucleus with formula (I);

$R_3$ represents a hydrogen atom, a $C_1$-$C_6$ alkyl group, or a phenyl group or its forms, with one of the $R_5$ or $R_6$ groups, a cycle C, which may or may not be aromatic, containing five to ten members, preferably six to seven members, which can optionally be substituted by one or more radicals $R^a$ as defined in claim 1; one of groups X, Y and Z represents N, O, S, Se or $NR_5$.

5. A compound according to claim 4 characterised in that in formula (II) or (III), cycle C represents benzene, cyclohexane or cycloheptane.

6. A compound according to claim 1 characterised in that the heterocycle H condensed at the 6,7 or 5,6 positions is selected from benzofuran, cycloheptanofuran, cyclohexanofuran, or pyrimidine, pyrazine, pyrrole, pyridine, oxazole or thiazole nuclei, which may be substituted.

7. A compound according to claim 1 characterised in that it comprises a heterocycle H containing five members condensed at the 5,6 or 6,7 positions on the benzopyrane nucleus of formula (I).

8. A compound according to claim 7 characterised in that it comprises a heterocycle H containing five members condensed at the 6,7 positions of the benzopyrane nucleus of formula (I).

9. A compound according to claim 1 characterised in that it is selected from one of the following formulae:

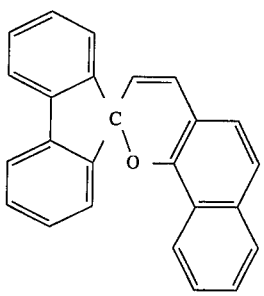 (A)

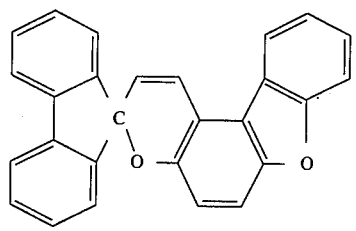 (B)

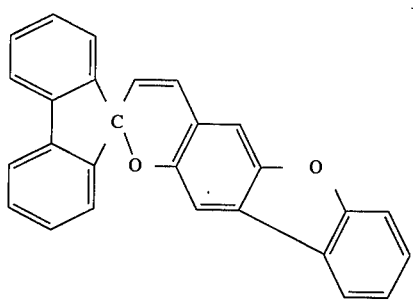 (C)

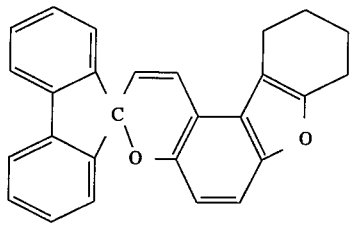 (D)

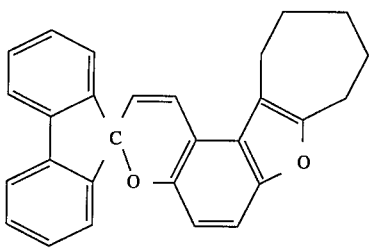 (E)

-continued

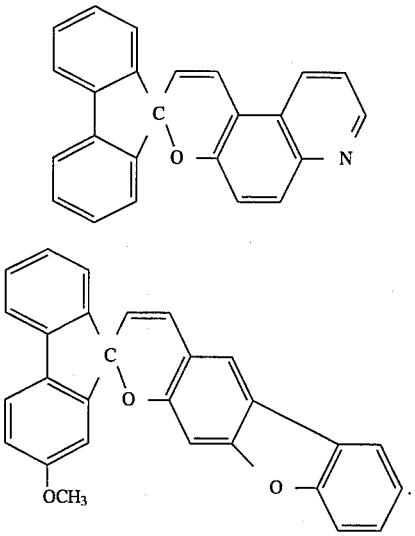

(F)

(G)

10. A composition for use on or introduction into a transparent organic polymeric material characterised in that it contains at least one photochromic compound as defined in claim 1 in sufficient quantities to cause the material to change colour on exposure to ultraviolet radiation.

11. A composition according to claim 10 characterised in that the composition is in a liquid form containing dissolved or dispersed photochromic compounds according to claim 1 in a medium based on appropriate solvents for application to or introduction into a transparent polymeric material.

12. A composition for application to or introduction into a transparent organic polymeric material characterised in that it is constituted by a colourless or transparent solution based on transparent polymers, copolymers or a mixture of polymers in an appropriate organic solvent, containing at least one photochromic compound as defined in claim 1 in sufficient quantities to cause the material to change colour on exposure to ultraviolet radiation.

13. A solid transparent material for producing ophthalmic lenses characterised in that it comprises at least one photochromic compound as defined in claim 1 in sufficient quantities to cause the material to change colour on exposure to ultraviolet radiation.

14. A transparent solid material according to claim 13 characterised in that it contains 0.01% to 20% by weight of photochromic compounds.

15. A composition or transparent solid material according to claim 10 characterised in that the photochromic compound as defined in any one of claims 1 to 9 is used jointly with other photochromic compounds which produce different colourations.

16. A transfer lacquer characterised in that it contains at least one compound as defined in claim 1.

17. An ophthalmic lens characterised in that it is formed from a transparent solid material as defined in claim 13.

18. A solid transparent material according to claim 13, wherein the at least one photochromic compound is disposed on a surface of the transparent material.

* * * * *